US006956134B2

(12) United States Patent
Liu et al.

(10) Patent No.: US 6,956,134 B2
(45) Date of Patent: Oct. 18, 2005

(54) OXIDATION OF METHANOL AND/OR DIMETHYL ETHER USING SUPPORTED MOLYBDENUM-CONTAINING HETEROPOLYACID CATALYSTS

(75) Inventors: Haichao Liu, Beijing (CN); Enrique Iglesia, Moraga, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/754,652

(22) Filed: Jan. 8, 2004

(65) Prior Publication Data

US 2005/0154226 A1 Jul. 14, 2005

(51) Int. Cl.⁷ .......................... C07C 45/29; C07C 67/00
(52) U.S. Cl. ...................... 568/472; 568/594; 560/131; 560/232
(58) Field of Search ................. 568/594, 472; 560/131, 232

(56) References Cited

U.S. PATENT DOCUMENTS

| | | | |
|---|---|---|---|
| 4,149,009 A | 4/1979 | Yoneoka et al. | |
| 4,216,339 A | 8/1980 | Couteau et al. | |
| 4,232,171 A | 11/1980 | Yoneoka et al. | |
| 4,319,037 A | 3/1982 | Yoneoka | |
| 4,480,122 A | 10/1984 | Horlenko et al. | |
| 4,757,044 A * | 7/1988 | Cooper et al. | 502/204 |
| 4,778,923 A | 10/1988 | Aplin et al. | |
| 4,994,603 A | 2/1991 | Mueller et al. | |
| 5,026,904 A | 6/1991 | Lodge et al. | |
| 5,144,062 A | 9/1992 | Chen et al. | |
| 5,194,675 A | 3/1993 | Joerg et al. | |
| 5,223,102 A | 6/1993 | Fedkiw, Jr. et al. | |
| 5,399,745 A | 3/1995 | Yoneoka et al. | |
| 5,401,873 A | 3/1995 | Zehner et al. | |
| 5,917,085 A | 6/1999 | Lippert et al. | |
| 6,379,507 B1 | 4/2002 | Satoh et al. | |

OTHER PUBLICATIONS

Liu et al. Site Titration with Organic Bases During Catalysis: Selectivity Modifier and Structral Probe in Methanol Oxidation on Keggin Clusters. Angew. Chem. Int. Ed. 2003, 42, p 5072-5075.*

Ai, M. et al., "The Production of Methyl Formate by the Vapor-Phase Oxidation of Methanol," *Journal of Catalysis*, 1982, pp. 279-288, vol. 77, Academic Press, Inc.

Liu, et al., "Selective Synthesis of Dimethoxymethane via Direct Oxidation of Methanol or Dimethylether on Supported Keggin Clusters," 18th North American Catalysis Society Meeting, Jun. 1, 2003, 78 pages, Cancun, Mexico.

Tronconi, E., et al., "Methyl Formate from methanol Oxidation over Coprecipitated V-Ti-O Catalysts," *Ind. Eng. Chem. Res.*, 1987, pp. 1269-1275, vol. 26, American Chemical Society.

Valente, N. G. et al., "Structure and acitivity of Sn-Mo-O Catalysts: partial oxidation of methanol," *Applied Catalysis A: General*, 2001, pp. 201-214, vol. 205, Elsevier Science B.V.

Yuan, Y., et al., "Performance and Characterization of a New Crystalline $SbRe_2O_6$ Catalyst for Selective Oxidation of Methanol to Methylal," *Journal of Catalysis*, 2000, pp. 51-61, vol. 195, Academic Press.

Yuan, Y., et al., "Performance and Characterization of Supported Rhenium Oxide Catalysts for Selective Oxidation of Methanol to Methylal," *J. Phys. Chem. B.*, 2002, pp. 4441-4449, vol. 106, American Chemical Society.

* cited by examiner

*Primary Examiner*—Johann Richter
*Assistant Examiner*—Sikarl A. Witherspoon
(74) *Attorney, Agent, or Firm*—Townsend and Townsend and Crew LLP

(57) ABSTRACT

Feeds comprising methanol, dimethyl ether or a mixture of the two are oxidized by contacting the feed with an oxygen-containing gas and a supported heteropolyacid catalyst containing molybdenum or molybdenum and vanadium. The primary products are methylal (dimethoxymethane) and methyl formate. Production of dimethyl ether from methanol can be inhibited by partial deactivation of acid sites on the Keggin catalyst.

34 Claims, 9 Drawing Sheets

*Figure 2.* Adsorption uptakes and DMM and DME synthesis rates as a function of time-on-stream during 2,6-di-tert-butyl-pyridine addition to $H_5PV_2Mo_{10}O_{40}/SiO_2$ (0.28 KU/nm$^2$, 453 K, 4 kPa $CH_3OH$, 9 kPa $O_2$, $CH_3OH$/2,6-di-tert-butyl-pyridine (mol) = 1110)
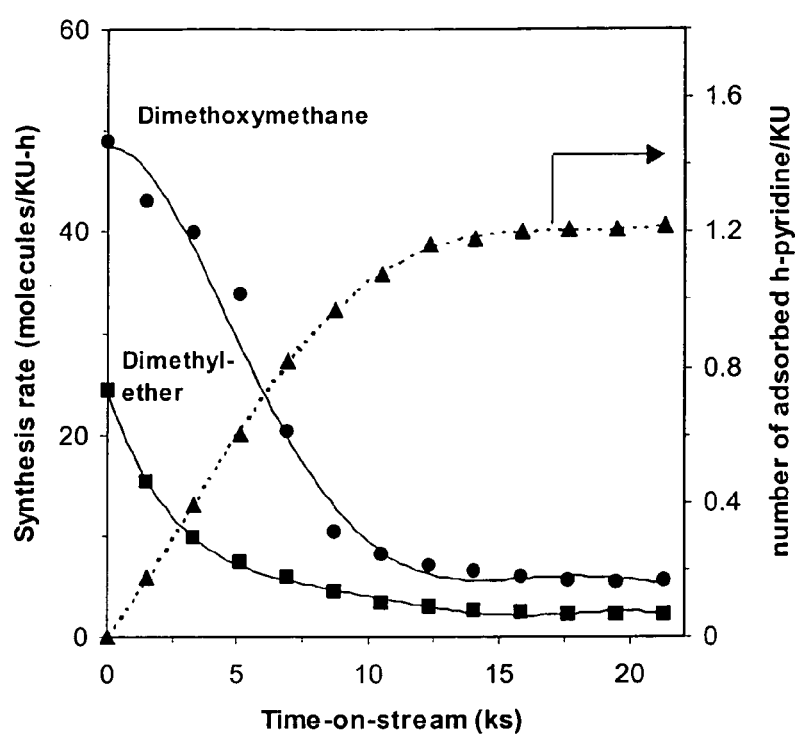

Figure 3. DMM synthesis rates as a function of the number of protons (per KU) titrated with 2,6-di-tert-butyl-pyridine on unsupported and $SiO_2$-supported (0.1-0.65 KU/nm$^2$) $H_5PV_2Mo_{10}O_{40}$ (453 K, 4 kPa $CH_3OH$, 9 kPa $O_2$, $CH_3OH$/2,6-di-tert-butyl-pyridine (mol) = 1110).
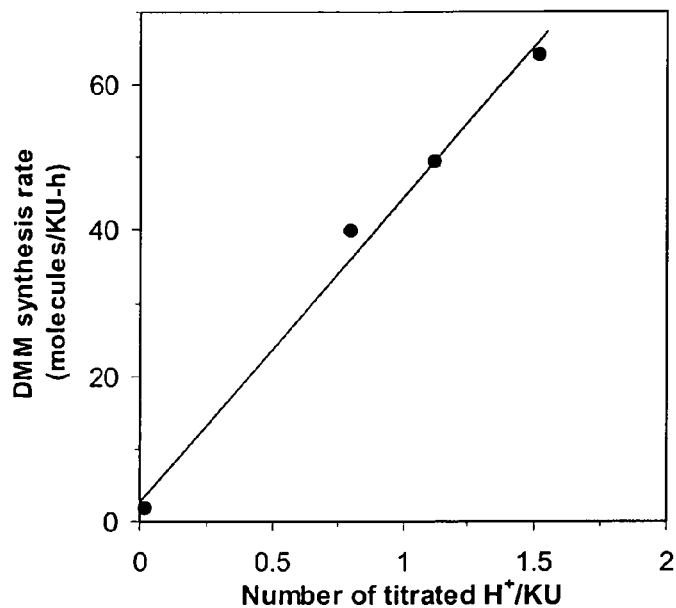

*Figure 4.* DMM and DME synthesis rates and their ratios of DMM/DME as a function of the number of protons (per KU) titrated by pyridine on $H_5PV_2Mo_{10}O_{40}/SiO_2$ (0.1 KU/nm$^2$, 453 K, 4 kPa $CH_3OH$, 9 kPa $O_2$, $CH_3OH$/pyridine (mol) = 800).
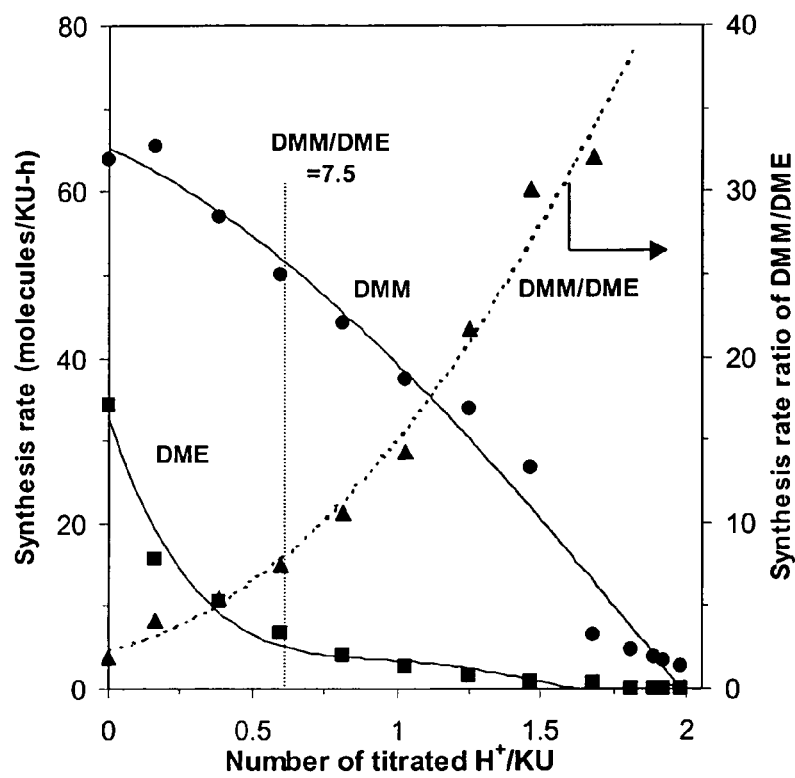

*Figure 5.* DMM and DME synthesis rates and their ratios of DMM/DME as a function of time-on-stream after titration of 0.6 H$^+$/KU and stop of pyridine injection on H$_5$PV$_2$Mo$_{10}$O$_{40}$/SiO$_2$ (0.1 KU/nm$^2$, 453 K, 4 kPa CH$_3$OH, 9 kPa O$_2$, CH$_3$OH/pyridine (mol).= 800).
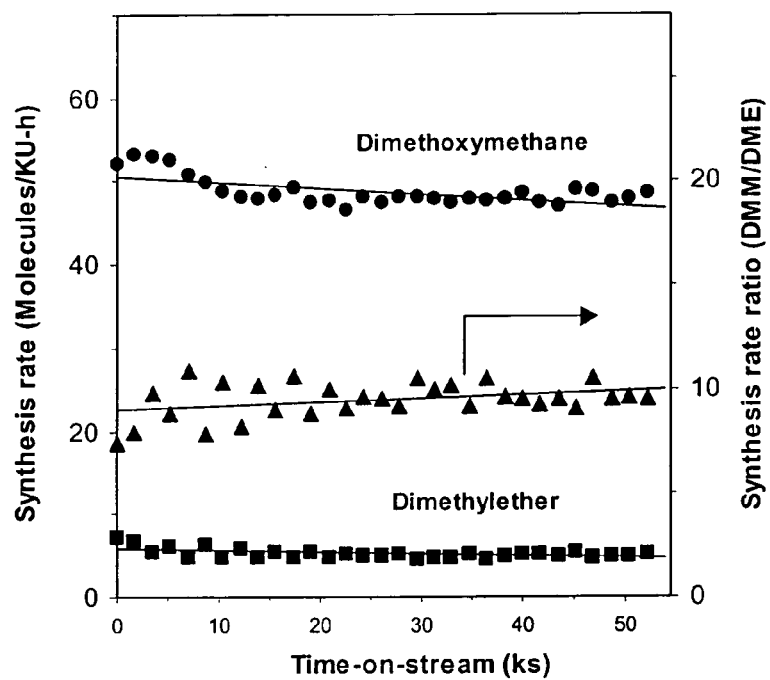

*Figure 6.* CH$_3$OH conversion rates (on a DME-free basis) and selectivities as a function of residence time at 493 K on H$_5$PV$_2$Mo$_{10}$O$_{40}$/ZrO$_2$ (0.31 KU/nm$^2$, 4 kPa CH$_3$OH, 9 kPa O$_2$, 1 kPa N$_2$, CH$_3$OH conversion: 18.6-65.8%).
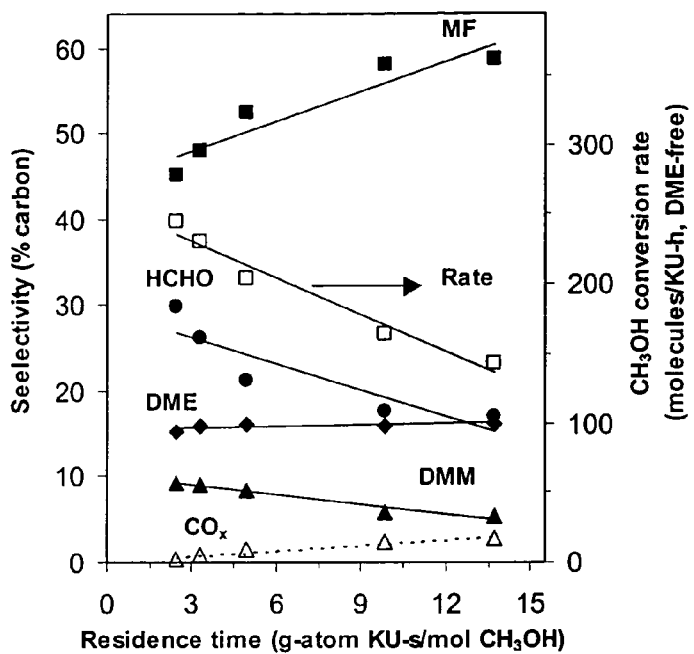

Figure 7. CH$_3$OH conversion rates (on a DME-free basis) and selectivities as a function of residence time at 493 K on H$_5$PV$_2$Mo$_{10}$O$_{40}$/SiO$_2$ (0.28 KU/nm$^2$, 4 kPa CH$_3$OH, 9 kPa O$_2$, 1 kPa N$_2$, CH$_3$OH conversion: 21.3-47.6%).
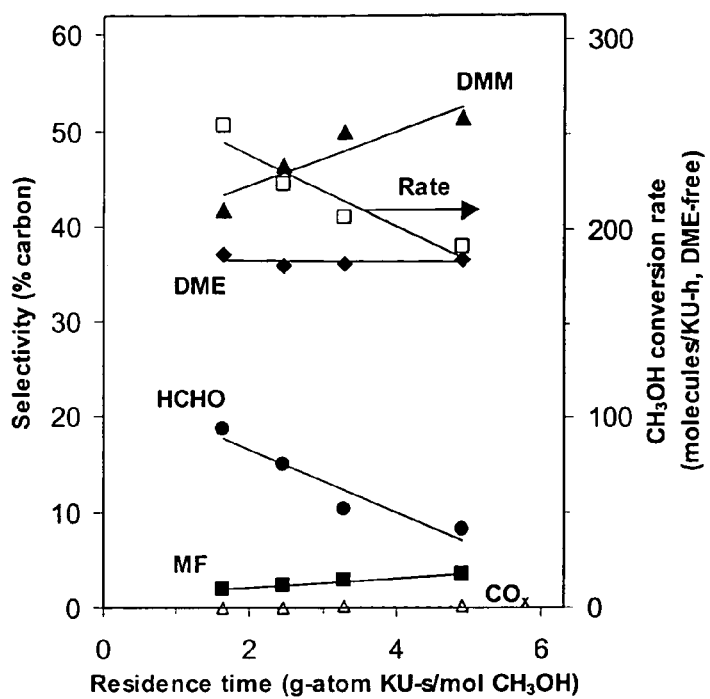

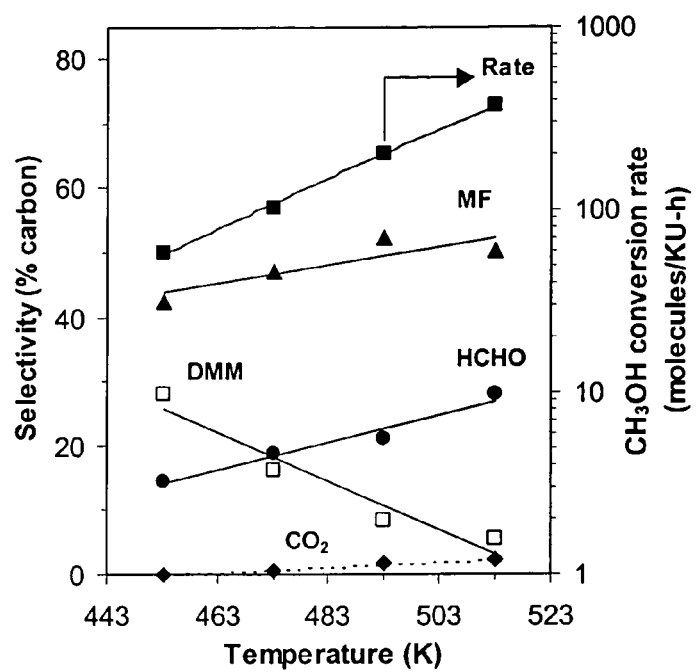
Figure 8. CH$_3$OH conversion rates (on a DME-free basis) and selectivities as a function of reaction temperature on H$_5$PV$_2$Mo$_{10}$O$_{40}$/ZrO$_2$ (0.31 KU/nm$^2$, 4 kPa CH$_3$OH, 9 kPa O$_2$, 1 kPa N$_2$, CH$_3$OH conversion: 14.5-51.2%).

OXIDATION OF METHANOL AND/OR DIMETHYL ETHER USING SUPPORTED MOLYBDENUM-CONTAINING HETEROPOLYACID CATALYSTS

FIELD OF THE INVENTION

This invention relates to a process for the oxidation of methanol, and optionally also of dimethyl ether, to produce a product that contains primarily methyl formate and/or dimethoxymethane (methylal), and to catalysts for use in that process.

Dimethoxymethane or methylal ($CH_3OCH_2OCH_3$) (often referred to as "DMM") is an important chemical intermediate. It is used as a gasoline additive, as a building block in organic syntheses, and as a precursor in the synthesis of concentrated formaldehyde streams and of polyoxymethylene dimethyl ethers useful as diesel fuel additives. DMM can be formed from formaldehyde produced via oxidation of methanol. However, attempts at developing a one-stage syntheses of DMM from $CH_3OH$, e.g.:

or from dimethyl ether (DME) have achieved only limited success. Current state-of-the-art DMM synthesis processes involve two stages—oxidation of methanol to formaldehyde on silver or iron molybdate catalysts, followed by subsequent condensation reactions of methanol-formaldehyde mixtures using sulfuric acid or solid acid catalysts.

Satoh et al. (U.S. Pat. No. 6,379,507) describe a liquid phase process for production of DMM or methylal from methanol, formaldehyde and water using a series of four reactors filled with an acid catalyst, preferably a cation exchange resin or a silica/alumina zeolite. A comparison example shows that all four reactors are needed for the process. Yuan et al., *J. Phys. Chem.* 2002, 106:4441 describes production of methylal by oxidation of methanol using a supported rhenium oxide catalyst. This was a single-stage process that showed excellent selectivity, though with methanol conversions below 50%. However, it involves drawbacks including the use of an expensive material as the catalyst coupled with volatility of rhenium oxide and significant loss of rhenium values at the operating temperature of the process (about 473–593 K). Earlier work by these researchers is reported in Yuan et al., *J. Catalysis* 2000, 195:51. U.S. Pat. No. 5,223,102 (Fedkiw, Jr., et al.) discloses a process for electrooxidation of methanol to produce formaldehyde and methylal.

Methyl formate is a significant chemical intermediate used for example as in the production of formic acid, dimethylformamide (DMF), and acetic acid. This compound is produced either by catalytic non-oxidative dehydrogenation of methanol or by reaction of methanol with carbon monoxide in the presence of a catalyst. Production of methyl formate by catalytic non-oxidative dehydrogenation of methanol has been described in a number of patents and articles, and using a variety of catalysts. Such processes typically result in production of dimethoxymethane, formaldehyde, and dimethyl ether, in addition to methyl formate. Temperatures, for the most part, run from about 180 to about 350° C.

For instance, U.S. Pat. No. 4,149,009 (Yoneoka et al.) describes such a process in which the catalyst contained copper, zirconium and zinc, and optionally aluminum, and in which a nonreactive gas such as hydrogen, carbon monoxide or nitrogen is employed. This process does not use oxygen as a co-reactant. The examples show operation at temperatures of from 230 to 330° C. Selectivity to methyl formate increased with increasing reaction time, often reaching above 90% after 50 hours or more. In U.S. Pat. No. 4,232,171 (also of Yoneoka et al.), describing a similar process, the catalyst contained a copper compound and cement. Temperatures were from 192 to 260° C. with selectivities to methyl formate reaching above 90% in one example. U.S. Pat. No. 4,319,037 (Yoneoka) describes such a non-oxidative process using a catalyst containing a copper compound and a compound of a Group IIIA or IVA metal. Temperatures ranged from 139 to 301° C. Methyl formate selectivities of up to 97% were achieved, though often the selectivity was accompanied by a low overall conversion of methanol.

U.S. Pat. No. 4,480,122 (Horlenko et al.) describes a process for non-oxidative dehydrogenation of methanol using copper-containing catalysts supported on spinels. Temperatures here were at higher levels of from 222 to 330° C. Selectivity to methyl formate was as low as 9% and as high as 91% with variations in the reaction conditions. In U.S. Pat. No. 4,778,923 (Aplin et al.) the catalyst in another such process was a platinum group metal, preferably a ruthenium-phosphine complex, and temperatures ranged from 148 to 180° C. Yields of methyl formate, however, were quite low, with hydrogen being the major reaction product. In U.S. Pat. No. 5,144,062 (Chen et al.) the catalysts for this reaction contained a copper oxide, a chromium oxide, and a sodium compound such as sodium oxide, hydroxide, carbonate or bicarbonate. Temperatures ranged from 140 to 180° C. Selectivity to methyl formate was high, ranging from 81.2 to as high as 97.8%. However, the yield of methyl formate in this process is generally below 50%, limited by the thermodynamics of the reaction.

U.S. Pat. No. 5,194,675 (Joerg et al.) discloses a non-oxidative dehydrogenation process in which the catalyst contained copper supported on magnesium silicate, optionally doped with one or more other metals. Process temperatures ranged from 160 to 260° C., with selectivity to methyl formate ranging from 48.1 to 98.0%. In U.S. Pat. No. 5,399,745 (Yoneoka et al.) the reaction was run in the liquid rather than gas phase at 195–199° C. using a copper-zinc-aluminum-containing catalyst. Methyl formate selectivities ranged from 74.8 to 92.5%.

Processes for production of methyl formate by reaction of methanol with carbon monoxide (i.e., carbonylation) are described, for instance, in U.S. Pat. No. 4,216,339 (Couteau et al.), U.S. Pat. No. 4,994,603 (Mueller et al.), U.S. Pat. No. 5,401,873 (Zehner et al.), and U.S. Pat. No. 5,917,085 (Lippert et al.). This processes, however, requires the handling of high pressures of carbon monoxide, a substance with significant implications for the metallurgy of the required reactors. U.S. Pat. No. 5,026,904 (Lodge et al.) discloses production of formates by reaction of hydrogen, carbon dioxide and an alcohol.

Production of methyl formate by oxidation of methanol with oxygen is also described in the technical literature. For example, Tronconi et al., *Ind. Eng. Chem. Res.* 1987, 26:1269 described such a reaction using a vanadium/titanium oxide catalyst with about 80% selectivity to methyl formate at 170° C. (443 K). In Ai, *J. Catal.* 1982, 77:279, the catalyst was a molybdenum/stannic oxide combination. Methyl formate selectivity was 90% at 160° C. (433 K). Valente et al., *Appl. Catal.* 2001, 205:201 also used a molybdenum/stannic oxide catalyst, at 180° C. (453 K). However, selectivity to methyl formate was low (47.0%) and a substantial conversion of methanol to dimethyl ether occurred concurrently (selectivity ~24.2%).

It thus would be desirable to provide a process for production of methyl formate or DMM/methylal from methanol with improved performance over the prior art. For DMM, such a process conducted in a single stage would be particularly desirable, but is currently unavailable. It would also be desirable to provide such a process that did not result in significant quantities of dimethyl ether. It also would be desirable to provide a process for production of methylal from dimethyl ether, which is less expensive to produce from synthesis gas than is methanol.

BRIEF SUMMARY OF THE INVENTION

This invention provides a process for oxidation of methanol, dimethyl ether, or a mixture of methanol and dimethyl ether, to methyl formate and/or methylal, comprising contacting the methanol, dimethyl ether, or a mixture thereof with an oxygen-containing gas and a supported heteropolyacid catalyst comprising molybdenum and optionally vanadium, said catalyst having a Keggin crystal structure (see Okuhara, et al., *Adv. Catal.* 1994, 41: 113). The support comprises silica and/or zirconia. Methyl formate is primarily produced when a catalyst supported on zirconia is used; methylal as the primary product is formed using a catalyst supported on silica. By "primarily" or "primary product" is meant that the product referred to is produced in greater quantities than others, although it might not necessarily constitute over 50% of the total reaction products. The catalyst may be treated to partially deactivate acid sites on the Keggin catalyst so as to decrease production of dimethyl ether in the process.

In another aspect this invention relates to a method or process for treating a molybdenum-containing heteropolyacid catalyst having a Keggin structure with an organic base, preferably a tertiary amine such as a pyridine, so as to partially deactivate acidic sites on the catalyst. In the context of the present invention this results in lower production of dimethyl ether as a byproduct of the methanol oxidation. In addition the catalysts of this invention enable the production of methylal from methanol with quite good selectivity and conversion (especially when considered on a dimethyl ether-free basis), and at comparatively low temperatures. The catalysts may also be used for production of methylal from dimethyl ether or from mixtures of dimethyl ether and methanol.

DESCRIPTION OF THE DRAWINGS

FIG. 2 shows adsorption uptakes and DMM and DME synthesis rates from methanol as a function of time-on-stream, with partial deactivation of acid sites on the $H_5PMo_{10}V_2O_{40}/SiO_2$ (0.28 KU/nm$^2$) catalyst using 2,6-di-tert-butyl-pyridine.

FIG. 3 shows DMM synthesis rates from methanol as a function of the number of protons (per KU) titrated with 2,6-di-tert-butyl-pyridine on unsupported and SiO$_2$-supported (0.1–0.65 KU/nm$^2$) $H_5PV_2Mo_{10}O_{40}$ catalysts.

FIG. 4 shows DMM and DME synthesis rates from methanol and their ratios of DMM/DME as a function of the number of protons (per KU) titrated by pyridine on $H_5PMo_{10}V_2O_{40}/SiO_2$ (0.10 KU/nm$^2$) catalyst.

FIG. 5 shows DMM and DME synthesis rates and their ratios of DMM DME as a function of time-on-stream after titration of 0.6H$^+$/KU followed by stopping of pyridine injection with $H_5PMo_{10}V_2O_{40}/SiO_2$ (0.10 KU/nm$^2$) catalyst.

FIG. 6 shows the effects of reactant residence time on methanol conversion rates and selectivities at 493 K on $H_5PMo_{10}V_2O_{40}/ZrO_2$ (0.31 KU/nm$^2$) catalyst.

FIG. 7 shows the effects of reactant residence time on methanol conversion rates and selectivities at 493 K on $H_5PMo_{10}V_2O_{40}/SiO_2$ (0.28 KU/nm$^2$) catalyst.

FIG. 8 shows the effects of reaction temperature on methanol conversion rates and selectivities at 493 K on $H_5PMo_{10}V_2O_{40}/ZrO_2$ (0.31 KU/nm$^2$) catalyst.

DETAILED DESCRIPTION

Figure 1A:
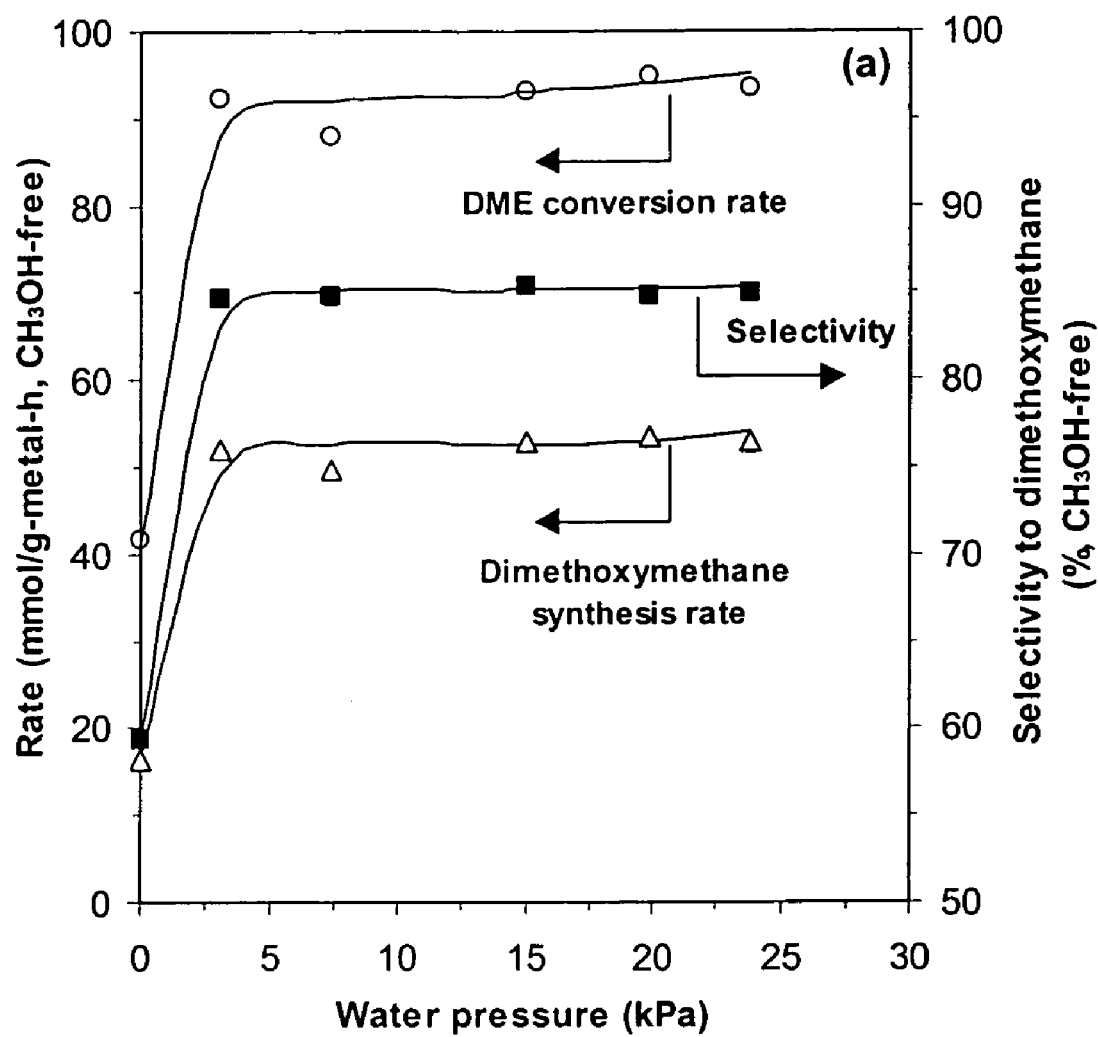
FIG. 1 shows the effect of addition of water in a process for oxidation of dimethyl ether (DME) using a catalyst of the invention, $H_5PMo_{10}V_2O_{40}/SiO_2$ (0.28 KU/nm$^2$).

This invention provides a process for production of a product containing primarily methyl formate and/or primarily methylal by catalytic oxidation of a methanol feed that optionally also contains dimethyl ether, or alternatively of a feed that comprises primarily dimethyl ether. The catalyst employed is a supported heteropolyacid catalyst comprising molybdenum and optionally vanadium, and that has a Keggin structure. The support comprises a particulate silica and/or zirconia. Preferably the catalyst is disposed on the surface of the support in a density that is approximately that of a monolayer of catalyst.

Keggin catalysts, generally, are heteropolyacid oxygen-containing catalysts having a central phosphorus or silicon atom that connects twelve peripheral octahedrally coordinated metal atoms. When the metal atoms are molybdenum atoms, the catalyst has the general formula $H_3XMo_{12}O_{40}$ where X stands for phosphorus or silicon. When the catalyst also includes vanadium, the overall formula becomes $H_{3+n}XV_nMo_{12-n}O_{40}$. In the process of this invention, X is preferably phosphorus and n is a value from 0 to 4. The process thus is one for the oxidation of methanol and/or dimethyl ether with an oxygen-containing gas and a supported heteropolyacid Keggin catalyst having the formula $H_{3+n}XV_nMo_{12-n}O_{40}$ where X represents phosphorus or silicon and n is a value of from 0 to 4. Keggin catalysts contain active acid sites as well as redox functionalities. Both properties are needed for production of methyl formate and methylal from methanol; however, the presence of the acid sites can also result in production of undesirable dimethyl ether by dehydration of the methanol, when methylal or methyl formate is the primary desired product.

In the processes of this invention a feed comprising methanol and/or dimethyl ether is contacted with a supported Keggin catalyst comprising molybdenum, and optionally vanadium, and in which the support comprises particulate silica and/or zirconia. The reaction temperature can range from about 160 to about 260° C., preferably from about 180 to about 220° C. The pressure is from about 0.5 to about 2000, preferably from about 2 to about 500 kPa. Space velocity is from about 30 to about 30,000 hr$^{-1}$, preferably from about 100 to about 10,000 hr$^{-1}$. Methanol concentration in the flow is from about 0.5 to about 99%, preferably from about 2 to about 90%.

As will be seen from the examples below, varying the process conditions, catalyst, and support can result in differences in conversion or selectivity, as well as in the nature of the primary product of the reaction. In general, when particulate silica is used as the support the primary product from methanol is DMM or methylal, whereas when particulate zirconia is the support, the primary product is methyl formate. When using a silica support, dimethyl ether can also be a significant component of the reaction product; however, the amount of dimethyl ether formed can be reduced by partially deactivating acid sites on the catalyst. When using a zirconia support, the production of dimethyl ether is not usually sufficiently great to be of concern, although if desired the catalyst may be subjected to partial deactivation of acid sites to reduce the formation of dimethyl ether to an even lower amount.

When the catalyst support is silica, the methanol conversion rate increases with increasing temperature, while selectivity to methylal decreases, with concomitant increase in the selectivity to formaldehyde at similar methanol conversion levels. When the catalyst is supported on particulate zirconia, methanol conversion rates and selectivity to methyl formate increase with increasing temperature, without significantly concomitant increase in production of carbon oxides ($CO+CO_2$) at similar methanol conversion levels. When the feed is primarily or only dimethyl ether, the inclusion of water in a dimethyl ether feed results in increased methylal synthesis rates due to an increase in the rate of dimethyl ether hydrolysis to methanol on $SiO_2$-supported catalysts.

The process for oxidation of methanol and/or dimethyl ether involves contacting that substance or substances with an oxygen-containing gas in the presence of a supported Keggin catalyst of the invention. The oxygen-containing gas used in the process may be in the form of molecular oxygen, a commercial mixture of molecular oxygen with an inert gas such as nitrogen, air, or oxygen-enriched air, but is preferably substantially pure oxygen or a commercial mixture that contains predominantly oxygen. The molar ratio of oxygen (calculated as $O_2$) to methanol and/or dimethyl ether is from about 0.05 to about 30, preferably from about 0.2 to about 10. Alternatively, an oxidizing agent such as hydrogen peroxide may be used for the reaction. The feed may comprise primarily or substantially only methanol, primarily or substantially only dimethyl ether, or a mixture of the two, particularly mixtures in which methanol or dimethyl ether is the major constituent and the other is present in a minor amount, for example as an impurity or a by-product from a previous step for production of the major constituent.

In practice, the processes of this invention may be run in equipment ranging in size from microreactors (e.g. microchannel reactors) to full-sized commercial process equipment. A commercial installation will include typical process expedients such as recycle streams, for efficient use of reactants and reaction products, and may be integrated with process units for production of products from the methyl formate and/or other products of the reaction. For example, if the process is aimed at producing methyl formate from methanol, dimethoxymethane in the reaction products may be recycled for production of additional methyl formate.

The catalysts used in the processes of this invention are heteropolyacid catalysts having a Keggin structure that comprise molybdenum or a combination of molybdenum and vanadium. The catalysts contain from about 0.05 to about 20, preferably from about 0.25 to about 10, weight % molybdenum and from about 0.01 to about 5, preferably from about 0.02 to about 0.1, weight % vanadium, based on total supported catalyst weight, if that substance is used in the catalyst. If the catalyst contains both molybdenum and vanadium, then the total metal content, based on total weight of the supported catalyst is from about 0.01 to about 20, preferably from about 0.25 to about 10, weight %. When the catalyst contains only molybdenum, it has the general formula $H_3XMo_{12}O_{40}$ where X stands for phosphorus or silicon. When the catalyst also includes vanadium oxide, the overall formula becomes $H_{3+n}XV_nMo_{12-n}O_{40}$ where n=0–4. In the process of this invention, X is preferably phosphorus and n is a value from 0 to 4.

The catalyst support comprises a particulate silica and/or zirconia, or it may be composed of a layer of zirconia deposited on particulate silica, especially a high surface area silica, to increase the available surface area of the zirconia per unit volume. In the catalysts of this invention, the heteropoly acids are distributed on the surface of the support material preferably with a surface density equal to or below that of a monolayer of the heteropoly acid. The surface density of heteropoly acids on the support is expressed as the number of Keggin units (KU) normalized per BET surface area (calculated from $N_2$ absorption at its normal boiling point using the Brunauer-Emmett-Teller, or BET, equation) of the catalyst ($KU/nm^2$).

The surface density of the catalyst can affect the catalyst efficiency. At one extreme, catalysts of this type have relatively few active sites on the support surface. These catalysts tend to interact with the support and lose proton sites, and thus provide lower reaction rates for oxidation to produce methyl formate or methylal per Keggin unit. At the other extreme, catalysts having a rather high density of Keggin units, or bulk (i.e., unsupported) Keggin catalysts lack efficiency in the utilization of Keggin structures because a substantial amount of the Keggin structures is located within crystals and is thus not available for catalyzing the reaction.

It has been found that the most preferred catalysts for this reaction tend to have a surface density of approximately a monolayer of catalyst on the support. The monolayer surface density for $H_5PV_nMo_{12-n}O_{40}$ (n=0–4) is approximately 0.7 $KU/nm^2$. The terms "monolayer" and "monolayer capacity value" as used herein are meant to refer to this value. A preferred range of surface densities is from about 3 to about 200%, preferably from about 10 to about 150%, of the monolayer capacity value for the supports usable in the catalysts of this invention.

The Keggin catalysts are prepared by typical means, for instance by impregnation, particularly incipient wetness impregnation, of the support with a methanolic solution of the heteropolyacid or acids. In a preferred embodiment the preparation is carried out so as to disperse the metal oxide or oxides over the surface of the support, and the amounts are chosen so as to achieve a desired surface density, as described above.

The supported catalysts may be treated in one of a number of ways to partially reduce or deactivate some active Bronsted acid sites of the Keggin catalyst. Such treatment has been found to result in a decrease of conversion of methanol to dimethyl ether as compared to untreated catalyst. Bronsted acid sites are required for methylal synthesis; therefore only a partial treatment of the catalyst is conducted, preferably one aimed at reducing no more than about 30% of the acidic sites.

This treatment of the catalyst may be done in one of several ways, including thermal treatment and titration with an organic base, and may be done prior to or during the conduct of the process.

Thermal treatment is carried out before conducting the process, and is done by heating the supported catalyst to a temperature of from about 473 K to about 673 K (200–400° C.), preferably from about 250 to about 350° C., for a period of from about 0.5 to about 3 hrs, preferably from about 1 to abut 1.5 hrs. Heating at above about 400° C. can begin to cause undesirable destruction of the Keggin structure, Titration of the acidic sites is done by controlled contacting of the supported catalysts with an organic base for a sufficient time and in a sufficient amount to achieve the desired partial deactivation of acidic sites. The organic base is preferably an amine such as trimethylamine, triethylamine or a pyridine, and is most preferably pyridine or a substituted pyridine such as 2,6-di-(t-butyl)pyridine. The contacting may be done prior to the use of the catalyst in conducting the oxidation process, or may be done during the conducting of the process by feeding the amine to the reaction zone, either concurrently with the feed or in a separate stream. If the amine is one that may become volatilized during the reaction, then the amine is introduced continuously in a controlled manner, for example by introduction into or with the methanol and/or dimethyl ether feed, so as to maintain the catalyst in a constant partially deactivated state.

Some of the Keggin catalysts so modified with an amine, particularly a tertiary amine such as a pyridine, so as to deactivate at most 30% of the acid sites, are novel catalysts. In addition to their use in the oxidation of methanol and/or dimethyl ether, Keggin catalysts that have been so modified with an amine are useful in catalyzing other processes or reactions where controlled densities and/or activities of redox and acid sites are needed, or at least advantageous. Such reactions include bifunctional reactions of alkanes, of alkenes, and of higher alcohols.

EXAMPLES

The following examples are offered to illustrate, but not to limit the claimed invention.

General Procedures:

Supported heteropolyacid catalysts were prepared by incipient wetness impregnation of $SiO_2$ (Cab-O-Sil) or $ZrO(OH)_2$ with methanolic (Merck, 99.98%) solutions of each heteropolyacid $[H_{3+x}PV_xMo_{12-x}O_{40} \cdot 30H_2O]$ (x=0,1,2,4); Japan New Metals Co.] at 298 K for 5 h. Impregnated samples were then dried in ambient air at 393 K overnight. Particulate $ZrO(OH)_2$ was prepared via hydrolysis of aqueous zirconyl cloride (0.98%, Aldrich) solutions at a PH of ~10 using $NH_4OH$ (14.8 N, Fisher Scientic), followed by filtering of precipitated powders and drying in ambient air at 393 K overnight.

Methanol or dimethyl ether reactions were carried out at 453–533 K in a fixed-bed quartz microreactor containing catalyst powders (0.1–0.3 g) diluted with ground quartz in order to prevent temperature non-uniformities. Samples were treated in flowing 20% $O_2$/He ($O_2$, Praxair, 99.999%; He, Airgas, 99.999%; 0.67 cm³/s) for 1.0 h before catalytic reaction measurements. The reactant mixture consisted of 80 kPa DME (Praxair, 99.5%), 18 kPa $O_2$ and 2 kPa $N_2$ (Praxair, Certified $O_2/N_2$ mixture) for DME reactions, and 4 kPa $CH_3OH$ (Merck, 99.98%), 9 kPa $O_2$, 1 kPa $N_2$ (Praxair, Certified $O_2/N_2$ mixture) and 86 kPa balance He (Airgas, 99.999%) for $CH_3OH$ oxidation reactions. $CH_3OH$ was introduced by bubbling He gas through a glass saturator filled with liquid $CH_3OH$. Homogeneous $CH_3OH$ reactions were not detected for the conditions used. Methanol or mixtures of methanol with pyridine (Fisher Scientific, 99.9%) or 2,6-di-tert-butyl pyridine (h-pyridine; Aldrich, 97%) at a molar ratio of $CH_3OH$/pyridine =800 or $CH_3OH$/h-pyridine=1110 were introduced by continuous injection using a syringe pump for titration experiments. All transfer lines between the reactor and gas chromatograph were kept above 393 K in order to avoid condensation of reaction products. Reactants and products were analyzed by on-line gas chromatography (Hewlett-Packard 6890GC) using a methyl-silicone capillary (HP-1 with 30 m×0.25×0.25 μm film thickness) column and a Porapak Q packed column (80–100 mesh, 1.82 m×3.18 mm) connected to flame ionization and thermal conductivity detectors, respectively. Selectivities are reported on a carbon basis as the percentage of the converted reactant appearing as a given product, and rates are reported as the number of methanol molecules converted into a given product per Keggin unit per hour.

Example 1

Catalytic Oxidation of Dimethyl Ether on Unsupported or SiO2-Supported Catalysts Table 1 shows dimethyl ether (DME) reaction rates and selectivities at 513 K, 80 kPa DME, and 20 kPa $O_2$ on unsupported and $SiO_2$-supported $H_3PMo_{12}O_{40}$ and $H_5PV_2Mo_{10}O_{40}$ catalysts (treated for 1 h at 553 K). On the unsupported samples, dimethoxymethane (DMM) was the most abundant reaction product. Reaction rates were normalized per Keggin unit (DME molecules/KU-h) or per gram of V and Mo (mmol/g-metal-h). Reaction rates and selectivities were calculated by considering methanol as a product and as a result are reported on a methanol-free basis. At similar DME conversions (~2%), reaction rates were about two times greater on $H_3PMo_{12}O_{40}$ than on $H_5PV_2Mo_{10}O_{40}$, but the latter was more selective to desired partial oxidation products HCHO (14.8% vs. 2.8%) and DMM (56.8% vs. 46.0%), and formed less carbon oxides ($CO_x$) (14.9% vs. 24.5%). Methyl formate (MF) selectivities were much higher on $H_3PMo_{12}O_{40}$ (16.7%) than on $H_5PV_2Mo_{10}O_{40}$ (0.3%).

As shown in Table 1, supporting $H_3PMo_{12}O_{40}$ ($PMo_{12}$) and $H_5PV_2Mo_{10}O_{40}$ ($PV_2Mo_{10}$) on $SiO_2$ led to significantly higher DME oxidation reaction rates, as expected from their greater accessibility compared with their respective crystalline bulk structures. At similar surface densities and DME conversions, $H_3PMo_{12}O_{40}$/$SiO_2$ showed higher DME reaction rates than $H_5PV_2Mo_{10}O_{40}$/$SiO_2$, but as in the case of the unsupported samples, $H_5PV_2Mo_{10}O_{40}$ clusters were more selective for DMM synthesis than $H_3PMo_{12}O_{40}$ structures. These supported catalysts showed much lower selectivities to $CO_x$ than the corresponding bulk samples. On both supported catalysts, HCHO selectivities (22 or 33.2%) were higher and DMM selectivities (44.6 or 55.0%) were slightly lower than in the respective bulk compounds.

TABLE 1

DME oxidation at 513 K on unsupported and $SiO_2$-supported heteropolyacid catalysts (80 kPa DME, 18 kPa $O_2$, 2 kPa $N_2$). Data collected after 1.5 h on-stream time

| Catalyst | [a]DME conversion (%) | [a]Rate (DME molecules/KU-h) | [a]Rate (mol DME/g-metal-h) | [a]Selectivity (%) | | | | |
|---|---|---|---|---|---|---|---|---|
| | | | | $CH_3OH$ | HCHO | MF | DMM | $CO_x$ |
| $H_3PMo_{12}O_{40}$ | 2.0 | 10.1 | 8.4 | 9.9 | 2.8 | 16.7 | 46.0 | 24.5 |
| unsupported | (1.8) | (9.2) | (7.6) | | (3.1) | (18.5) | (51.1) | (27.2) |
| $H_5PV_2Mo_{10}O_{40}$ | 1.8 | 4.4 | 4.2 | 13.1 | 14.8 | 0.3 | 56.8 | 14.9 |
| unsupported | (1.6) | (3.8) | (3.6) | | (17.0) | (0.3) | (65.4) | (17.1) |
| $H_3PMo_{12}O_{40}/SiO_2$ | 2.3 | 125.3 | 103.5 | 6.3 | 22.0 | 15.0 | 44.6 | 9.4 |
| (9.3 wt %) | (2.2) | (117.4) | (96.9) | | (23.5) | (16.0) | (47.6) | (10.0) |
| $H_5PV_2Mo_{10}O_{40}/$ | 1.8 | 47.7 | 45.5 | 7.4 | 33.2 | 2.6 | 55.0 | 1.8 |
| $SiO_2$ (9.2 wt %) | (1.7) | (44.2) | (42.1) | | (35.9) | (2.8) | (59.4) | (1.9) |

[a]Data in the parentheses are calculated on a $CH_3OH$-free basis.

Figure 1B:
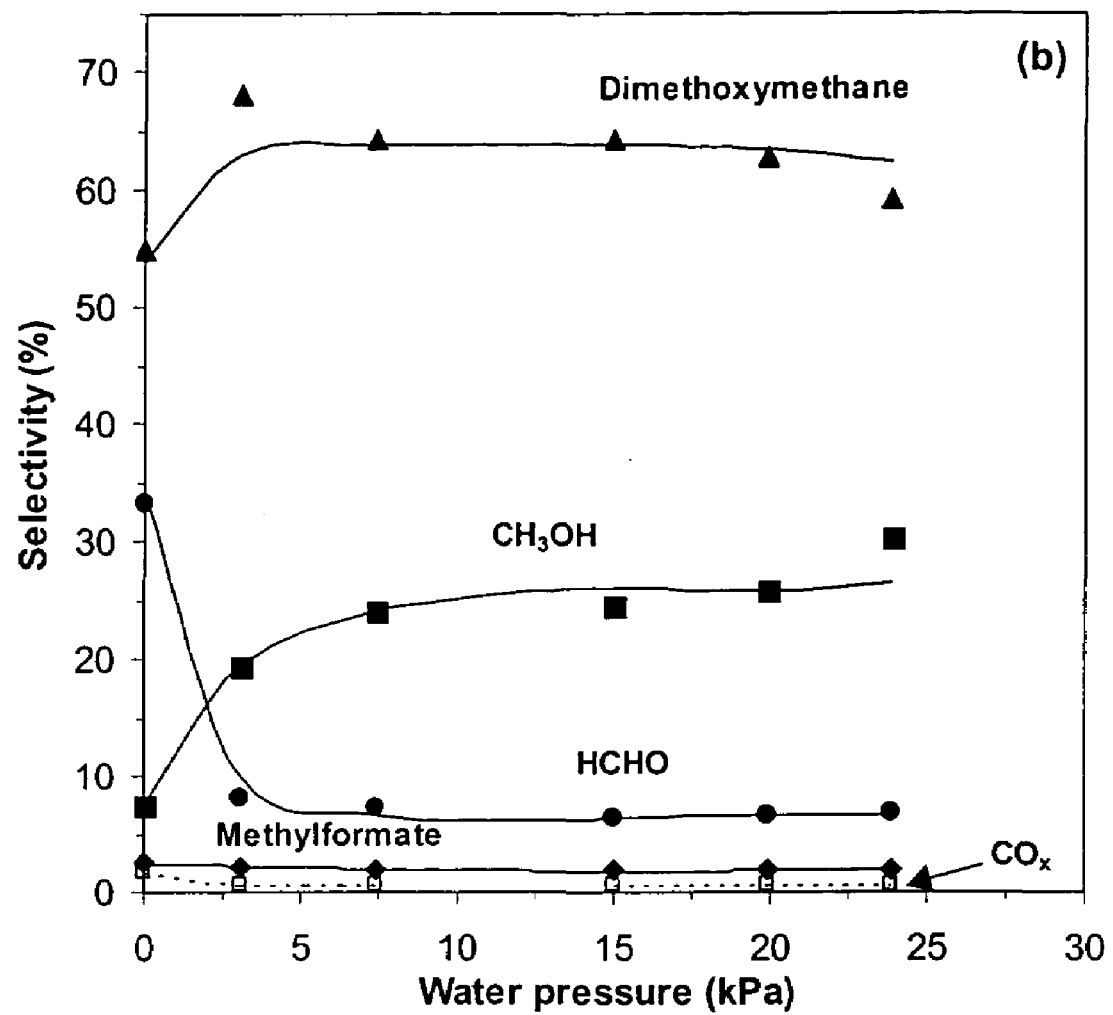

FIG. 1 shows the effect of adding water to DME reactants during reactions on $H_5PV_2Mo_{10}O_{40}/SiO_2$ (9.2 wt %; pretreated at 553 K). DME conversion rates and DMM synthesis rates increased by factors of two and three, respectively, and the DMM selectivity increased from 55.0% to 68.3% (59.4% to 84.6%, methanol-free basis) as 3.1 kPa water was added to the $DME/O_2$ reactant stream. The selectivity to methanol increased concurrently from 7.4% to 19.3% with increasing water concentration (FIG. 1b). Higher water concentrations led to additional small increases in DME rates. The selectivity to DMM increased from 59.4% to 84.6% ($CH_3OH$-free basis) as the $H_2O$ partial pressure increased to 3.1 kPa, but then remained essentially unchanged (84.7–85.3%) for higher $H_2O$ partial pressures (3.1–23.9 kPa; FIG. 1a). Similar $H_2O$ effects were observed on $H_3PMo_{12}O_{40}/SiO_2$.

Example 2

Catalytic Oxidation of Methanol on Unsupported or $SiO_2$-Supported Catalysts

Table 2 shows $CH_3OH$ conversion rates (DME-free) and selectivities obtained at 493 K on unsupported and $SiO_2$-supported $H_{3+n}PV_nMo_{12-n}O_{40}$ (n=0,1,2,4) catalysts. These materials were treated in dry air for 1 h at 553 K. The effect of this thermal pretreatment in deactivating acid sites is described below. Reaction rates are reported normalized per Keggin unit (molecules/KU-h) and per gram of the active element (mmol/g-metal-h). Again, selectivities are reported both by considering DME as a product and also on a DME-free basis. The main products formed from $CH_3OH$ oxidation on $H_{3+n}PV_nMo_{12-n}O_{40}$ catalysts (n=0,1,2,4) were HCHO, dimethoxymethane, methyl formate, and DME. At these conditions, $CO_x$ selectivities were very low (<5%) even at $CH_3OH$ conversions of nearly 70%. At similar $CH_3OH$ conversions, reaction rates on the unsupported heteropolyacids were only weakly influenced by the V/Mo content. DMM was the predominant product of oxidative $CH_3OH$ reactions on all three unsupported catalysts and DMM selectivities reached values of 75–81% (DME-free basis at 22–25% $CH_3OH$ conversion).

The replacement of some Mo atoms by V to form $H_4PVMo_{11}O_{40}$ and $H_5PV_2Mo_{10}O_{40}$ led to higher DMM selectivities and to lower MF selectivities, as shown in Table 2. The combined selectivity to desired DMM and HCHO products reached values as high as 95% at $CH_3OH$ conversions of 22% (both DME-free basis). High DME selectivities (~50%) were also observed on all crystalline bulk heteropolyacid samples.

In tests using supported catalysts, also as shown in Table 2, $CH_3OH$ conversion rates increased by a factor of ~40 (both per Keggin unit and per mass of active component). $H_4PVMo_{11}O_{40}$ clusters supported on $SiO_2$ were slightly more active than supported $H_3PMo_{12}O_{40}$, $H_5PV_2Mo_{10}O_{40}$, and $H_6PV_4Mo_8O_{40}$ clusters. The selectivity to DME was lower on supported catalysts than on unsupported catalysts. DMM selectivities of ~84% were reached on both $H_5PV_2Mo_{10}O_{40}/SiO_2$ and $H_4PVMo_{11}O_{40}/SiO_2$ samples at $CH_3OH$ conversions of 40.9–47.0%, with extremely low $CO_x$ selectivities (0.4–1.5%).

TABLE 2

$CH_3OH$ oxidation on unsupported and $SiO_2$-supported heteropolyacid catalysts at 493K[a]; comparison with reported results for other catalysts. Data collected after 1.5 h on-stream time

| Catalyst | [b]Conversion (%) | Rate (DME-free) (molecules/KU-h) | Rate (mmol/g-metal-h) | [b]Selectivity (%) | | | | |
|---|---|---|---|---|---|---|---|---|
| | | | | DME | HCHO | MF | DMM | $CO_x$ |
| $H_3PMo_{12}O_{40}$ | 52.6 | 6.2 | 5.1[c] | 52.2 | 4.2 | 4.2 | 34.6 | 5.0 |
| | (24.6) | | | | (8.8) | (9.3) | (72.3) | (10.4) |
| $H_4PVMo_{11}O_{40}$ | 44.2 | 5.3 | 4.8[c] | 52.1 | 6.5 | 0.7 | 38.8 | 1.7 |
| | (21.2) | | | | (13.6) | (1.4) | (81.1) | (3.5) |
| $H_5PV_2Mo_{10}O_{40}$ | 41.6 | 5.5 | 5.2[c] | 48.1 | 8.7 | 0.4 | 40.2 | 2.6 |
| | (22.4) | | | | (16.8) | (0.8) | (77.5) | (5.0) |

TABLE 2-continued

CH$_3$OH oxidation on unsupported and SiO$_2$-supported heteropolyacid catalysts at 493K[a]; comparison with reported results for other catalysts. Data collected after 1.5 h on-stream time

| Catalyst | [b]Conversion (%) | Rate (DME-free) (molecules/ KU-h) | Rate (mmol/g-metal-h) | [b]Selectivity (%) | | | | |
|---|---|---|---|---|---|---|---|---|
| | | | | DME | HCHO | MF | DMM | CO$_x$ |
| H$_3$PMo$_{12}$O$_{40}$/SiO$_2$ (9.3 wt %) | 68.5 (45.7) | 248.7 | 205.7[c] | 33.3 | 7.6 (11.4) | 11.9 (17.9) | 41.0 (61.5) | 5.5 (8.3) |
| H$_4$PVMo$_{11}$O$_{40}$/SiO$_2$ (9.2 wt %) | 68.2 (47.0) | 254.2 | 232.0[c] | 31.1 | 3.2 (4.6) | 5.6 (8.1) | 58.1 (84.3) | 1.0 (1.5) |
| H$_5$PV$_2$Mo$_{10}$O$_{40}$/SiO$_2$ (9.2 wt %) | 63.3 (40.9) | 217.4 | 206.8[c] | 35.4 | 4.5 (6.9) | 4.0 (6.2) | 54.0 (83.6) | 0.3 (0.4) |
| H$_6$PV$_4$Mo$_8$O$_{40}$/SiO$_2$ (10.2%) | 60.3 (41.8) | 143.9 | 154.2 | 30.7 | 10.7 (15.4) | 2.4 (3.5) | 55.1 (79.5) | 0 |
| [d]SbRe$_2$O$_6$ | 6.5 | — | ~1.1 | 6.5 | 0 | 1.2 | 92.5 | 0 |
| [e]ReO$_x$/Fe$_2$O$_3$ (10 wt Re %) | 48.4 | — | 319.2 | 1.0 | 2.4 | 4.6 | 91.0 | 1.0 |
| [f]PMo/SiO$_2$ (5.75 wt Mo %) | — | — | — | ~7 | ~16 | ~20 | ~55 | ~2 |

[a]Reactant mixture: 4 kPa CH$_3$OH, 10 kPa O$_2$, balance He.
[b]Data in the parentheses are calculated on DME-free basis.
[c]Data are calculated on a DME-free basis.
[d]Reaction mixture: CH$_3$OH/O$_2$/He = 4.0/9.7/86.3 (mol %); reaction temperature: 573 K. [Yuan et al., J. Catal. 2000, 195, 51]
[e]Reaction mixture: CH$_3$OH/O$_2$/He = 4.0/9.7/86.3 (mol %); reaction temperature: 513 K. [Yuan et al., J. Phys. Chem. B 2002, 106, 4441]
[f]Reaction mixture: CH$_3$OH/O$_2$/He = 4.5/10.3/85.2 (mol %); reaction temperature: 513 K; catalysts treated at 593 K. [Rocchiccioli-Deltcheff et al., J. Mol. Catal. 1996, 114, 331]

The above Table 2 also contains comparisons with results reported in the literature for oxidation of methanol using other catalysts, as indicated. The best reported catalysts for direct CH$_3$OH oxidation to DMM were based on supported Re oxides. However, CH$_3$OH reaction rates (per gram active component, DME-free basis) measured on H$_4$PVMo$_{11}$O$_{40}$/SiO$_2$ and H$_5$PV$_2$Mo$_{10}$O$_{40}$/SiO$_2$ catalysts of this invention are similar to the highest values reported on supported ReO$_x$ catalysts (Table 2). DMM selectivities were also similar when compared on a DME-free basis, but the large number of acid sites and strong acidity of heteropolyacid materials led to higher DME selectivities during CH$_3$OH reactions. Evaluation of some of the ReO$_x$-based compositions reported in CH$_3$OH reactions led to significantly higher DME selectivities than previously reported. It also led to the extensive sublimation of ReO$_x$ species, consistent with the high volatility of the prevalent ReO$_x$ species at the required reaction conditions.

Example 3

Effects of Surface Density on Reaction Rate and Selectivity on H$_5$PV$_2$Mo$_{10}$O$_{40}$/SiO$_2$ Catalysts Table 3 shows the effects of H$_5$PV$_2$Mo$_{10}$O$_{40}$ loading and surface density on the rate and selectivity of CH$_3$OH oxidation reactions. Surface densities are reported as the number of Keggin units or the number of V and Mo active metal atoms per BET surface area (KU/nm$^2$ and metal/nm$^2$). For loadings less than 9.2 wt %, reaction rates remained nearly constant with loading. Higher surface densities led to a decrease in CH$_3$OH reaction rates (per KU), perhaps because of incipient agglomeration of dispersed Keggin units into clusters with secondary crystalline structures. The samples with the lowest surface density (0.024 KU/nm$^2$) gave very low DME selectivity (20.4%) and high HCHO selectivity. Increasing the surface density to 0.10 KU/nm$^2$ led to higher DME and DMM selectivities and lower HCHO selectivities. At surface densities of 0.65 KU/nm$^2$, DMM selectivities decreased and HCHO selectivities increased. It appears that protons are consumed in condensation reactions leading to the anchoring of Keggin clusters at low H$_5$PV$_2$Mo$_{10}$O$_{40}$ surface densities and that the Keggin clusters may behave similarly to bulk H$_5$V$_2$Mo$_{10}$O$_{40}$ crystallites as surface densities increase beyond monolayer coverages.

Example 4

Thermal Pretreatment of Catalysts for Partial Deactivation of Acid Sites

It was found that a controlled thermal treatment of the Keggin catalysts of this invention, namely a thermal treatment at a temperature of up to about 673K can improve selectivity to DMM and reduce formation of DME. As is known in the art, Keggin clusters dehydroxylate via condensation reactions that convert OH groups into H$_2$O and form Mo—O—Mo linkages between Keggin units, ultimately destroying the primary Keggin structure to form crystalline MoO$_3$. These reactions occur between 550–670 K for bulk H$_5$PV$_2$Mo$_{12}$O$_{40}$. The effects of thermal pretreatment on CH$_3$OH reaction rate and selectivity on supported H$_5$PV$_2$Mo$_{10}$O$_{40}$ were explored. Results are shown in Table 3. Thermal treatments of H$_5$PV$_2$Mo$_{10}$O$_{40}$/SiO$_2$ (20.1 wt %) in air at 523 K led to high DME selectivities (46.2%) and to relatively low DMM selectivities of 37.1% (69.0%, DME-free), which is not the desired outcome of this process. However, as the thermal treatment temperature increased to 553 K, the DME selectivity declined to 36.5%, while the DMM selectivity increased to 51.2% (80.6%, DME-free). This trend continued until the treatment temperatures reached about 673 K. After treatment at 673 K, the DME selectivity was 13.4%, and the DMM selectivity was 70.5% (81.4%, DME-free). Further increases in the thermal treatment temperature (873 K) led to a sharp decrease in DMM selectivity and to a concurrent increase in HCHO selectivity, again, not an objective of this process. The reaction rates (DME-free) decreased from 185.4 mmol/g-metal-h to 143.0 mmol/g-metal-h by only about 20% as the treatment temperature increased from 553 K to 673 K, but then decreased sharply to 92.4 mmol/g-metal-h after treatment at 873 K.

This phenomenon appears to reflect the loss of protons via dehydroxylation and the consequent formation of condensed Keggin structures after thermal treatment at 523–673 K. Raman spectral analyses showed that after exposure of the material treated at 673K to ambient moisture, the original spectrum in the starting material was restored. This indicates that dehydroxylation processes are reversible at these temperatures and that destruction of the Keggin structure and formation of crystalline $MoO_3$ does not occur upon dehydroxylation at 673 K or lower temperatures in these samples. On the other hand, thermal treatments at 873 K led to the destruction of the Keggin structure in $H_5PV_2MoO_{40}$ and to the irreversible formation of $MoO_3$ crystallites, which remained after exposure to ambient moisture.

Example 5

Reactant Concentration and Temperature Effects on $CH_3OH$ Conversion to Dimethoxymethane on $H_5PV_2Mo_{10}O_{40}/SiO_2$ Table 4 shows the effects of reaction temperature on $CH_3OH$ conversion rates and selectivities on $H_5PV_2Mo_{10}O_{40}/SiO_2$ (9.2 wt %) samples treated at 553 K. Rates and selectivities are compared at similar $CH_3OH$ conversion levels (~27%, DME-free), which were achieved by varying reactant space velocities over a broad range. $CH_3OH$ reaction rates increased from 68 mmol/g-metal-h to 340 mmol/g-metal-h as reaction temperatures increased from 453 K to 513 K. DMM selectivities decreased from 91.8% (DME-free) to 51.1% in this temperature range, mostly as a result of a concurrent increase in HCHO selectivity with increasing reaction temperature. DME and MF selectivities were only weakly affected by reaction temperature.

TABLE 3

Effects of $H_5PV_2Mo_{10}O_{40}\cdot 30H_2O$ content of $H_5PV_2Mo_{10}O_{40}/SiO_2$ on $CH_3OH$ oxidation (493 K, 4 kPa DME, 9 kPa $O_2$, balance He).

| Content | SA | SD | SD | [a]Conversion | Rate (DME-free) | Rate (DME-free) | [a]Selectivity (%) | | | | |
|---|---|---|---|---|---|---|---|---|---|---|---|
| (wt %) | (m$^2$/g) | KU/nm$^2$ | Mo + V/nm$^2$ | (%) | (molecules/KU-h) | (mmol/g-metal-h) | DME | HCHO | MF | DMM | CO$_x$ |
| 2.5 | 271.1 | 0.024 | 0.3 | 27.2 (21.6) | 210.8 | 201.8 | 20.4 | 21.4 (26.9) | 4.6 (5.8) | 52.7 (66.3) | 0 |
| 5.1 | 263.3 | 0.051 | 0.6 | 33.7 (22.0) | 210.8 | 201.0 | 34.7 | 14.9 (22.8) | 4.2 (6.4) | 45.8 (70.1) | 0 |
| 9.2 | 236.2 | 0.10 | 1.2 | 44.5 (28.9) | 230.7 | 219.2 | 35.0 | 7.2 (11.1) | 3.1 (4.8) | 53.0 (81.6) | 0.1 (0.2) |
| 20.1 | 190.5 | 0.28 | 3.3 | 41.3 (26.2) | 190.9 | 181.9 | 36.5 | 8.1 (12.8) | 2.7 (4.3) | 51.2 (80.6) | 0 |
| 35.0 | 143.1 | 0.65 | 7.8 | 36.9 (23.9) | 150.0 | 142.7 | 35.2 | 16.8 (25.9) | 2.9 (4.5) | 43.4 (67.0) | 1.1 (1.6) |

[a]Data in the parentheses are calculated on DME-free basis.

TABLE 4

Effects of reaction temperature on $CH_3OH$ oxidation on $H_5PV_2Mo_{10}O_{40}/SiO_2$ (9.2 wt %, 4 kPa DME, 9 kPa $O_2$; catalyst sample treated in dry air at 553 K).

| Temperature | [a]Conversion | Rate (DME-free) | [a]Selectivity (%) | | | | |
|---|---|---|---|---|---|---|---|
| (K) | (%) | (mmol/g-metal-h) | DME | HCHO | MF | DMM | CO$_x$ |
| 453 | 39.9 (26.9) | 68.0 | 32.7 | 2.1 (3.1) | 3.2 (4.8) | 61.8 (91.8) | 0 |
| 473 | 39.3 (26.1) | 132.0 | 33.6 | 4.2 (6.3) | 3.3 (5.0) | 57.9 (87.2) | 0 |
| 493 | 45.2 (28.9) | 219.2 | 35.0 | 7.2 (11.1) | 3.1 (4.8) | 53.0 (81.6) | 0.1 (0.2) |
| 513 | 42.4 (27.3) | 340.4 | 36.0 | 24.6 (38.4) | 3.8 (6.0) | 32.7 (51.1) | 0.5 (1.9) |

[a]Data in the parentheses are calculated on DME-free basis.

Example 6

Controlled Deactivation of Acidic Sites on the Catalysts by Titration with an Amine Selective titration of the Keggin catalysts used in this invention with an organic base, here represented by pyridine and 2,6-di-(t-butyl)pyridine, partially deactivates Brönsted acid sites on the catalyst, leading to exceptionally high selectivity to DMM and decreased selectivity to DME. In the same experiments the base titration was also used to measure dispersion of Keggin structures on the support.

The dispersion of Keggin structures was measured by titration of Bronsted acid sites with 2,6-di-tert-butyl-pyridine, a sterically hindered pyridine, during catalytic reactions of $CH_3OH$—$O_2$ reactant mixtures. This 2,6-di-tert-butyl-pyridine titrant can be protonated on Brönsted acid sites, but it cannot interact with Lewis acid sites because of steric constraints near the N-atom. Its essentially hydrophobic character also prevents its dissolution and migration into secondary structures of Keggin clusters, in contrast with pyridine, which dissolves and penetrates into these secondary structures. Thus, 2,6-di-tert-butyl-pyridine uptakes during $CH_3OH$ reactions (per KU) reflect the number of accessible protons, and for a given $H_{3+n}PV_nMo_{12-n}O_{40}$ stoichiometry, the fraction of the Keggin structures accessible at external surfaces in supported and unsupported secondary structures.

The number of 2,6-di-tert-butyl-pyridine molecules adsorbed during $CH_3OH$—$O_2$ reactions at 453 K on $H_5PV_2Mo_{10}O_{40}/SiO_2$ (0.28 $KU/nm^2$ surface density on $SiO_2$) increased with time and reached saturation at 1.2$H^+$/KU after about 12 ks (kiloseconds) (FIG. 2). This corresponds to a nominal fractional dispersion of 0.24, in view of the $H^+$/KU expected stoichiometry of 5.

As shown in FIG. 3, $H^+$/KU ratios decreased from 1.6 to 0.7, corresponding to a decrease in nominal KU dispersion from 0.32 to 0.15, as KU surface densities on $SiO_2$ increased from 0.1 $KU/nm^2$ to 0.65 $KU/nm^2$ on $H_5PV_2Mo_{10}O_{40}/SiO_2$ samples. This ratio was 0.02$H^+$/KU for bulk $H_5PV_2Mo_{10}O_{40}$. DMM synthesis rates (per KU) decreased in parallel with this decrease in fractional KU dispersion as the surface density increased from 0.1 $KU/nm^2$ to 0.65 $KU/nm^2$ (FIG. 2). This correlation between rates and titrant uptakes for all samples, which include an unsupported version of this Keggin composition, indicates that 2,6-di-tert-butyl-pyridine predominately titrates those Keggin structures available for bifunctional DMM synthesis pathways.

The rates per KU for both bifunctional DMM and monofunctional DME syntheses decreased as 2,6-di-tert-butyl-pyridine titrated $H^+$ sites in $H_5PV_2Mo_{10}O_{40}/SiO_2$ (FIG. 2); they reached non-zero constant values after saturation adsorption of 2,6-di-tert-butyl-pyridine (1.2 per KU) (FIG. 2). Titration of protons led to lower DME selectivities, but the small number of residual protons untitrated by 2,6-di-tert-butyl-pyridine prevented the attainment of DME selectivities lower than 25%.

The effect of titration with pyridine, which can penetrate secondary Keggin structures, was then studied. This property makes pyridine unsuitable for KU dispersion measurements, but on the other hand makes it a more effective titrant to suppress residual DME synthesis pathways.

FIG. 4 shows DMM and DME synthesis rates at 453 K and their ratio on $H_5PV_2Mo_{10}O_4O/SiO_2$ (0.1 $KU/nm^2$) as a function of the number of $H^+$/KU titrated by pyridine. HCHO and MF products also were detected, at low selectivities (<4%). Titration with pyridine during reaction decreased both DME and DMM synthesis rates, but DMM/DME rate ratios increased from 1.9 to 7.5 as the number of titrated protons increased from 0 to 0.6 $H^+$/KU. In effect, the loss of acid sites by titration of 0.6$H^+$/KU led to relatively small changes in DMM synthesis rates (from 63.9 to 49.9 $(KU-h)^{-1}$), but decreased DME synthesis rates by more than a factor of five (34.2 to 6.6 $(KU-h)_{-1}$). Both DME and DMM reaction products became undetectable after titration of ~2.0$H^+$/KU, at which point all sites accessible to the reactants had been titrated by pyridine.

These data thus confirm that the number of Brönsted acid sites can be systematically controlled by controlled partial titration of Keggin structures, with marked and beneficial consequences for the selectivity of bifunctional redox-acid catalytic reactions.

These specific results for $H_5PV_2Mo_{10}O_{40}/SiO_2$ are representative of those obtained for other V/Mo ratios (0–0.5) and KU surface densities and dispersions (see Table 5). In all cases, the titration of 0.5–0.9$H^+$/KU using pyridine significantly decreased DME synthesis rates (by factors of 4.5–8), while decreasing DMM synthesis rates comparatively only slightly (by factors of 1.2–1.3). These combined effects led to much greater DMM selectivities (DMM/DME ratios>6) than on each corresponding composition unmodified by pyridine titrants (DMM/DME ratios ~2).

TABLE 5

DMM and DME synthesis rates and (DMM/DME) rate ratios on $SiO_2$-supported $H_{3+n}PV_nMo_{12-n}O_{40}$ (n = 0, 1, 2, 4; ~0.1 $KU/nm^2$) and $H_5PV_2Mo_{10}O_{40}/SiO_2$ with varying Keggin unit (KU) surface densities (0.1–0.65 $KU/nm^2$) before and after titration of 0.5–0.9 $H^+$/KU.[a]

| Catalyst ($KU/nm^2$) | Before titration (molecules/KU-h) | | | After titration (molecules/KU-h) | | |
|---|---|---|---|---|---|---|
| | DMM | DME | DMM/DME | DMM | DME | DMM/DME |
| $H_3PMo_{12}O_{40}$ (0.1) | 60.7 | 35.7 | 1.7 | 43.1 | 7.0 | 6.2 |
| $H_4PVMo_{11}O_{40}$ (0.1) | 72.6 | 31.5 | 2.3 | 51.7 | 6.4 | 8.1 |
| $H_5PV_2Mo_{10}O_{40}$ (0.1) | 63.9 | 34.2 | 1.9 | 49.9 | 6.6 | 7.5 |
| $H_6PV_4Mo_8O_{40}$ (0.1) | 43.4 | 20.7 | 2.1 | 33.5 | 4.7 | 7.1 |
| $H_5PV_2Mo_{10}O_{40}$ (0.28) | 49.3 | 25.4 | 1.9 | 39.8 | 6.2 | 6.4 |
| $H_5PV_2Mo_{10}O_{40}$ (0.65) | 40.8 | 26.1 | 1.6 | 27.2 | 3.1 | 8.8 |

[a]453 K, 4 kPa $CH_3OH$, 9 kPa $O_2$, $CH_3OH$/pyridine (mol) = 800, balance He; ~17–22% $CH_3OH$ conversion.

The resulting titrated catalysts are organic-inorganic composite materials whose use in this reaction can produce high selectivity to DMM (>80%) and low DME (<12%) selectivity, without a significant decrease in DMM yields over those obtained without pyridine titrants.

In addition, the change in the catalyst resulting from such titration appears to be a permanent one. FIG. 5 shows DMM and DME synthesis rates on $H_5PV_2Mo_{10}O_{40}/SiO_2$ (0.1 $KU/nm^2$) for a period of 15 h after cessation of pyridine introduction after ~0.6$H^+$/KU titration by pyridine. DMM and DME synthesis rates did not change during catalytic $CH_3OH$—$O_2$ reactions during this time. It seems clear therefore that pyridine-KU hybrid structures remain unchanged during reaction, and that titration is permanent under these reaction conditions. Similar stability was confirmed by us for other Keggin compositions.

Example 7

Catalytic Oxidation of Methanol on $H_5Mo_{10}V_2O_{40}$ Supported on Different Supports Table 6 shows methanol conversion rates and selectivities on $H_5PV_2Mo_{10}O_{40}$ supported on $ZrO_2$, $SiO_2$, $TiO_2$ and $Al_2O_3$ at 393 K. This comparison is made on samples with similar densities of Keggin units (0.28–0.37 $KU/nm^2$) and also at similar $CH_3OH$ conversion levels (30–40%); relative contributions from primary and secondary reactions depend on residence time and conversion, as discussed below. Reaction rates reported in Table 6 are normalized per Keggin unit and reported on a DME-free basis (conversion to all products except DME). Pure $Al_2O_3$ supports formed only DME, while other pure supports did not form any products at detectable rates. $CH_3OH$ conversion rates were slightly higher when $H_5PV_2Mo_{10}O_{40}$ clusters were supported on $ZrO_2$ and $TiO_2$ than when supported on $SiO_2$, and were much lower when supported on $Al_2O_3$ (Table 6).

tion of the $H_5PV_2Mo_{10}O_{40}$ Keggin clusters on these different supports, which were probed by organic base titration (i.e. 2,6-di-tert-butyl pyridine) and Raman spectroscopy, respectively.

Example 8

Catalytic Oxidation of Methanol on Physical Mixtures of Supported $H_5PV_2Mo_{10}O_{40}$ Catalysts and Pure Supports The role of the supports in determining the product mixture was examined using mixtures of supported

TABLE 6

Methanol oxidation rates, selectivities and number of accessible Bronsted acid sites on $H_5PV_2Mo_{10}O_{40}$ supported on $ZrO_2$, $TiO_2$, $SiO_2$ and $Al_2O_3$ (treated at 553 K) and on pure supports (493 K, 4% $CH_3OH$, 9% $O_2$, 1% $N_2$, He balance, 30–40% $CH_3OH$ conversion)

| Catalyst | Surface density ($KU/nm^2$) | Rate (DME-free) (molecules/KU-h) | ODH rate (molecules/KU-h) | Selectivity (% carbon) | | | | |
|---|---|---|---|---|---|---|---|---|
| | | | | DME | HCHO | MF | DMM | $CO_x$ |
| $H_5PV_2Mo_{10}O_{40}/ZrO_2$ | 0.31 | 213.7 | 127.8 | 16.1 | 21.2 | 52.4 | 8.3 | 2.0 |
| $H_5PV_2Mo_{10}O_{40}/SiO_2$ | 0.28 | 190.9 | 79.7 | 36.5 | 8.1 | 2.7 | 51.2 | 0 |
| $H_5PV_2Mo_{10}O_{40}/TiO_2$ | 0.37 | 195.2 | 146.0 | 9.5 | 53.2 | 30.2 | 7.1 | 0 |
| $H_5PV_2Mo_{10}O_{40}/Al_2O_3$ | 0.35 | 51.2 | 41.3 | 71.1 | 19.2 | 5.1 | 4.6 | 0 |
| $ZrO_2$ | — | trace | — | — | — | — | — | — |
| $SiO_2$ | — | trace | — | — | — | — | — | — |
| $TiO_2$ | — | trace | — | — | — | — | — | — |
| $Al_2O_3$ | — | [a]26.0 | — | 100 | 0 | 0 | 0 | 0 |

[a]$CH_3OH$ conversion rate: mmol/g-$Al_2O_3$-h at 34% $CH_3OH$ conversion.

The identity of the support influences $CH_3OH$ reaction selectivities on $H_5PV_2Mo_{10}O_{40}$ clusters. On $SiO_2$, DMM is the main product (51.2%) along with DME (36.5%), while MF is formed with very low selectivity (2.7%). In marked contrast, MF became the predominant product (52.4%) and DMM selectivities were very low (8.3%) when $ZrO_2$ was used as the support instead of $SiO_2$ (Table 6). DME selectivities were much lower on $H_5PV_2Mo_{10}O_{40}/ZrO_2$ than on $SiO_2$-supported samples (16.1% vs. 36.5%). On $TiO_2$ supports, $H_5PV_2Mo_{10}O_{40}$ clusters predominantly formed HCHO (53.2%); the MF selectivity was 30.2% with very low DME and DMM selectivities (9.5% and 7.1%, respectively). $CH_3OH$ dehydration to DME became the predominant reaction (~71% selectivity) on $H_5PV_2Mo_{10}O_{40}/Al_2O_3$, as expected from the reactivity of Brönsted or Lewis acid sites on pure $Al_2O_3$ supports for bimolecular $CH_3OH$ dehydration reactions. These support effects are consistent with the observed change in the acidity and the structural evolution $H_5PV_2Mo_{10}O_{40}$ catalysts with additional amounts of pure supports of a different nature. As shown in Table 7, the addition of $ZrO_2$ to $H_5PV_2Mo_{10}O_{40}/SiO_2$ (3:1 mass ratio) at 493 K increased MF selectivity from 2.7 to 42.3%, while DMM selectivity decreased from 51.2 to 8.9%. Addition of $TiO_2$ to $H_5PV_2Mo_{10}O_{40}/SiO_2$ (3:1 mass ratio) led to MF and DMM selectivities of 29.2% and 17.8% (vs. 2.7% and 51.2%), respectively. The stronger effects of $ZrO_2$ relative to $TiO_2$ as an additive is consistent with the higher MF selectivities obtained when the former is used directly as the support for Keggin clusters (Table 6). When pure $SiO_2$ (3:1 mass ratio) was added to $H_5PV_2Mo_{10}O_{40}/ZrO_2$, DMM selectivities increased from 8.3% to 19.1%. None of the experiments in which additional amounts of pure supports were added led to detectable increases in the rates for oxidative dehydrogenation (ODH) of $CH_3OH$ to HCHO (Table 7).

TABLE 7

Methanol oxidation rates and selectivities on physical mixtures of $H_5PV_2Mo_{10}O_{40}/SiO_2$ + $ZrO_2$, $H_5PV_2Mo_{10}O_{40}/SiO_2$ + $ZrO_2$, and $H_5PV_2Mo_{10}O_{40}/SiO_2$ + $ZrO_2$ at a mass ratio of 1/3, and for comparison on $H_5PV_2Mo_{10}O_{40}/SiO_2$ (0.28 $KU/nm^2$) and $H_5PV_2Mo_{10}O_{40}/ZrO_2$ (0.31 $KU/nm^2$) treated at 553 K (493 K, 4% $CH_3OH$, 9% $O_2$, 1% $N_2$, 30–40% $CH_3OH$ conversion).

| Catalyst (mass ratio) | Conversion rate (DME-free) (molecules/KU-h) | ODH rate (molecules/KU-h) | Selectivity (% carbon) | | | | |
|---|---|---|---|---|---|---|---|
| | | | DME | HCHO | MF | DMM | $CO_x$ |
| $H_5PV_2Mo_{10}O_{40}/SiO_2$ + $ZrO_2$ (1/3) | 174.3 | 83.9 | 35.4 | 7.0 | 42.3 | 8.9 | 6.4 |

TABLE 7-continued

Methanol oxidation rates and selectivities on physical mixtures of $H_5PV_2Mo_{10}O_{40}/SiO_2$ + $ZrO_2$, $H_5PV_2Mo_{10}O_{40}/SiO_2$ + $ZrO_2$, and $H_5PV_2Mo_{10}O_{40}/SiO_2$ + $ZrO_2$ at a mass ratio of 1/3, and for comparison on $H_5PV_2Mo_{10}O_{40}/SiO_2$ (0.28 $KU/nm^2$) and $H_5PV_2Mo_{10}O_{40}/ZrO_2$ (0.31 $KU/nm^2$) treated at 553 K (493 K, 4% $CH_3OH$, 9% $O_2$, 1% $N_2$, 30–40% $CH_3OH$ conversion).

| Catalyst | Conversion rate (DME-free) | ODH rate | Selectivity (% carbon) | | | | |
|---|---|---|---|---|---|---|---|
| (mass ratio) | (molecules/KU-h) | (molecules/KU-h) | DME | HCHO | MF | DMM | $CO_x$ |
| $H_5PV_2Mo_{10}O_{40}/ZrO_2$ + $SiO_2$ (1/3) | 211.3 | 122.9 | 15.3 | 19.1 | 50.2 | 14.1 | 1.3 |
| $H_5PV_2Mo_{10}O_{40}/SiO_2$ + $TiO_2$ (1/3) | 168.7 | 85.5 | 33.3 | 14.5 | 29.2 | 17.8 | 5.2 |
| $H_5PV_2Mo_{10}O_{40}/SiO_2$ | 190.9 | 79.7 | 36.5 | 8.1 | 2.7 | 51.2 | 0 |
| $H_5PV_2Mo_{10}O_{40}/ZrO_2$ | 213.7 | 127.8 | 16.1 | 21.2 | 52.4 | 8.3 | 2.0 |

Example 9

Effects of Residence Time on Reaction Rates and Selectivities

FIG. 6 shows the effects of reactant residence time, changed by varying the space velocity, on methanol conversion rates and selectivities at 493 K on $H_5PV_2Mo_{10}O_{40}/ZrO_2$ (0.31 $KU/nm^2$). Rates decreased with increasing residence time and methanol conversion. MF selectivities increased with increasing residence time and methanol conversion, while HCHO and DMM selectivities decreased. $CO_x$ selectivities remained very low (0–2.5%), but increased with increasing the residence time. DME selectivities were essentially unchanged by residence time. FIG. 7 shows similar residence time effects on $H_5PV_2Mo_{10}O_{40}/SiO_2$ (0.28 $KU/nm^2$). On this catalyst, DMM selectivities increased monotonically with residence time. The effects of residence time on the $CH_3OH$ conversion rate and the selectivities to other products (HCHO, MF, $CO_x$ and DME) on $H_5PV_2Mo_{10}O_{40}/SiO_2$ are similar to those on $H_5PV_2Mo_{10}O_{40}/ZrO_2$.

Example 10

Effects of Surface Density of Keggin Structures Supported on $ZrO_2$ on $CH_3OH$ Reaction Rates and Selectivities The catalytic properties of the $H_5PV_2Mo_{10}O_{40}$ Keggin clusters depend on their surface densities, which were varied by changing the amount deposited on $ZrO_2$ supports. As shown in Table 8, methanol conversion rates and the calculated ODH rates for $CH_3OH$ to HCHO increased by a factor of ca. 2.2 and 2.5, respectively, as the surface density increased from 0.08 to 0.31 $KU/nm^2$. MF selectivities decreased from 77.6% to 52.4% as the Keggin cluster surface density increased in this range. The slight increase in the $H^+/KU$ number (from 0.68 to 0.93$H^+/KU$; measured by the saturated 2,6-tert-butyl pyridine uptakes) led to the concurrent increase in the selectivities of DME and DMM (Table 8), consistent with the acid site requirement for their formation.

TABLE 8

Methanol conversion rates (DME-free basis), selectivities and number of accessible Bronsted acid sites as a function of $H_5PV_2Mo_{10}O_{40}$ surface density on $ZrO_2$ (493 K, 4% $CH_3OH$, 9% $O_2$, 1% $N_2$, 30–40% $CH_3OH$ conversion).

| Surface density | Bronsted acid sites | Conversion rate (DME-free) | ODH rate | Selectivity (% carbon) | | | | |
|---|---|---|---|---|---|---|---|---|
| ($KU/nm^2$) | ($H^+/KU$) | (molecules/KU-h) | (molecules/KU-h) | DME | HCHO | MF | DMM | $CO_x$ |
| 0 | — | Trace | Trace | — | — | — | — | — |
| 0.08 | 0.68 | 97.8 | 52.0 | 9.8 | 7.6 | 77.6 | 2.8 | 2.3 |
| 0.15 | 0.84 | 145.6 | 76.8 | 10.4 | 8.9 | 72.8 | 5.9 | 2.1 |
| 0.31 | 0.92 | 213.7 | 127.8 | 16.1 | 21.2 | 52.4 | 8.3 | 2.0 |

Example 11

Effects of Reaction Temperature on $CH_3OH$ Reaction Rates and Selectivities on $H_5PV_2Mo_{10}O_{40}/ZrO$ FIG. 8 shows the effects of reaction temperature on $CH_3OH$ conversion rates and selectivities. The rates increased from 58.6 to 373.7 molecules/KU-h on $H_5PV_2Mo_{10}O_{40}/ZrO_2$ (0.31 $KU/nm^2$) as the temperature increased from 453 K to 513 K at similar $CH_3OH$ conversions (30–40%). HCHO and MF selectivities increased from 13.5% to 27.9% and 42.5% to 52.4%, respectively, with increasing the temperature in this temperature range, while the DMM selectivities decreased from 28.4% to 5.6%. Selectivities to by-products DME (~15%) and COX (<2.2%) were only weakly affected by reaction temperature (FIG. 8).

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A process for the oxidation of a feed comprising methanol and/or dimethyl ether to produce a product containing primarily methylal or primarily methyl formate, comprising contacting the feed with an oxygen-containing gas and a supported heteropolyacid Keggin catalyst having the formula $H_{3+n}XV_nMo_{12-n}O_{40}$ where X represents phosphorus or silicon and n is a value of from 0 to 4.

2. A process according to claim 1 comprising oxidation of methanol.

3. A process according to claim 2 in which the product comprises primarily methylal.

4. A process according to claim 2 in which the product comprises primarily methyl formate.

5. A process according to claim 4 in which the product additionally comprises methylal and/or formaldehyde.

6. A process according to claim 1 comprising oxidation of dimethyl ether.

7. A process according to claim 1 comprising oxidation of a mixture of methanol and dimethyl ether.

8. A process according to claim 1 in which the oxygen-containing gas is selected from oxygen, air, oxygen-enriched air, and mixtures of oxygen with inert gases.

9. A process according to claim 1 in which the catalyst support comprises particulate silica.

10. A process according to claim 1 in which the catalyst support comprises zirconia.

11. A process according to claim 1 in which the catalyst support comprises particulate zirconia.

12. A process according to claim 1 in which the catalyst support comprises a layer of zirconia deposited on a particulate silica.

13. A process according to claim 1 in which the surface density of the heteropolyacid catalyst on the support is from about 3% to about 200% of the surface density of a monolayer of said catalyst.

14. A process according to claim 1 in which the surface density of the heteropolyacid catalyst is approximately that of a monolayer of said catalyst.

15. A process according to claim 1 in which n is 0.

16. A process according to claim 1 in which n is 1.

17. A process according to claim 1 in which n is 2.

18. A process according to claim 1 in which n is 4.

19. A process according to claim 1 comprising oxidation of methanol, in which the catalyst support comprises particulate silica and the primary product is methylal.

20. A process according to claim 1 comprising oxidation of methanol, in which the catalyst support comprises particulate zirconia and the primary product is methyl formate.

21. A process according to claim 1 in which the temperature is from about 160 to about 260° C.

22. A process according to claim 1 in which the temperature is from about 180 to about 220° C.

23. A process according to claim 1 in which the catalyst is supported on a particulate silica, wherein the catalyst is treated, prior to or during the process, so as to partially deactivate acid sites.

24. A process according to claim 23 in which the catalyst is treated to deactivate up to 30% of the acid sites.

25. A process according to claim 23 in which the catalyst is treated to partially deactivate acid sites by heating the supported catalyst to a temperature of from about 200 to about 400° C. for a time of from about 0.2 to about 2 hr prior to conducting the oxidation process.

26. A process according to claim 23 in which the catalyst is treated to partially deactivate acid sites by contacting the catalyst with an amine.

27. A process according to claim 26 in which the catalyst is contacted with the amine prior to conducting the oxidation process.

28. A process according to claim 26 in which the catalyst is contacted with the amine during the oxidation process.

29. A process according to claim 28 in which the catalyst is continuously contacted with the amine during the oxidation process.

30. A process according to claim 29 in which the amine is fed to the process concurrently with the methanol and/or dimethyl ether.

31. A process according to claim 26 in which the amine is a tertiary amine.

32. A process according to claim 26 in which the amine is pyridine or a substituted pyridine.

33. A process according to claim 26 in which the amine is pyridine.

34. A process according to claim 26 in which the amine is 2,6,-di-(tert-butyl) pyridine.

* * * * *